United States Patent [19]

Codina et al.

[11] Patent Number: 5,668,309

[45] Date of Patent: Sep. 16, 1997

[54] CAPACITIVE PARTICLE SENSOR

[75] Inventors: George Codina, North Hollywood, Calif.; Chandrasekar Ramamoorthy, Normal; Donna J. Murr, Dunlap, both of Ill.

[73] Assignee: Caterpillar Inc., Peoria, Ill.

[21] Appl. No.: 521,861

[22] Filed: Aug. 31, 1995

[51] Int. Cl.[6] .............................. G01N 15/06; H04N 5/21
[52] U.S. Cl. .................... 73/61.71; 324/71.1; 324/663; 324/672; 340/627
[58] Field of Search .................. 73/61.71; 324/663, 324/672, 71.1, 71.2; 340/627

[56] References Cited

U.S. PATENT DOCUMENTS

| | | |
|---|---|---|
| 3,233,173 | 2/1966 | Lees et al. .............................. 324/663 |
| 3,595,078 | 7/1971 | Beck et al. . |
| 3,635,082 | 1/1972 | Prellwitz et al. . |
| 3,802,261 | 4/1974 | Zimmerman et al. . |
| 4,074,184 | 2/1978 | Dechene et al. . |
| 4,240,028 | 12/1980 | Davis, Jr. . |
| 4,266,188 | 5/1981 | Thompson . |
| 4,302,754 | 11/1981 | Magee et al. ........................ 324/235 X |
| 4,336,493 | 6/1982 | Gregory et al. ......................... 324/663 |
| 4,370,611 | 1/1983 | Gregory et al. ......................... 324/663 |
| 4,433,286 | 2/1984 | Capots et al. ............................ 324/663 |
| 4,468,611 | 8/1984 | Tward . |
| 4,604,904 | 8/1986 | Massen . |
| 4,658,208 | 4/1987 | Lee et al. . |
| 4,713,603 | 12/1987 | Thom . |
| 4,714,048 | 12/1987 | Jefferies et al. . |
| 4,751,842 | 6/1988 | Ekrann et al. . |
| 4,894,604 | 1/1990 | Dowling et al. . |
| 4,920,795 | 5/1990 | Codazzi et al. . |
| 5,382,942 | 1/1995 | Raffa et al. . |
| 5,418,468 | 5/1995 | Baker et al. .............................. 324/663 |

FOREIGN PATENT DOCUMENTS

| | | | |
|---|---|---|---|
| 944404 | 12/1963 | United Kingdom ................... 324/663 |
| 257 | 5/1979 | WIPO ...................................... 324/663 |

OTHER PUBLICATIONS

SAE Technical Paper Series—910497 Feb. 25–Mar. 1, 1991 "A Capacitive Oil Deterioration Sensor".

*Primary Examiner*—Hezron E. Williams
*Assistant Examiner*—Daniel S. Larkin
*Attorney, Agent, or Firm*—James R. Yee

[57] ABSTRACT

An apparatus for detecting particles within a hydraulic system having a hydraulic line includes a capacitor formed by a pair of electrodes. A charging circuit produces a charging current of constant magnitude. The charging current is used to charge the capacitor to a predetermined voltage. A timing circuit measures the elapsed time between the time at which the charging circuit begins to produce the charging current and the time at which the capacitor has been charged to the predetermined voltage. The timing circuit produces a pulse width modulated signal. The magnitude of the pulse width modulated signal is indicative of the time difference. A controller receives the pulse width modulated signal and detects particles by comparing the duration of each pulse with a reference pulse.

1 Claim, 2 Drawing Sheets

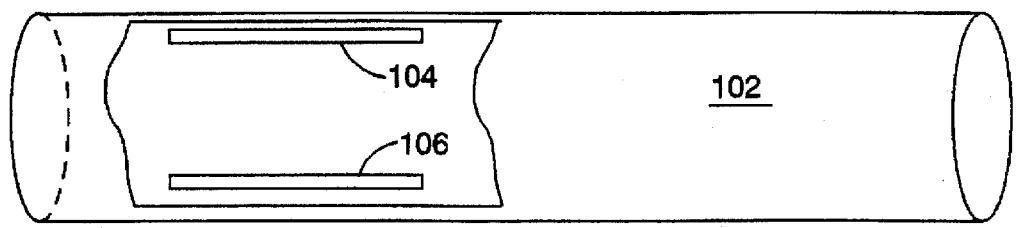
Fig_1_
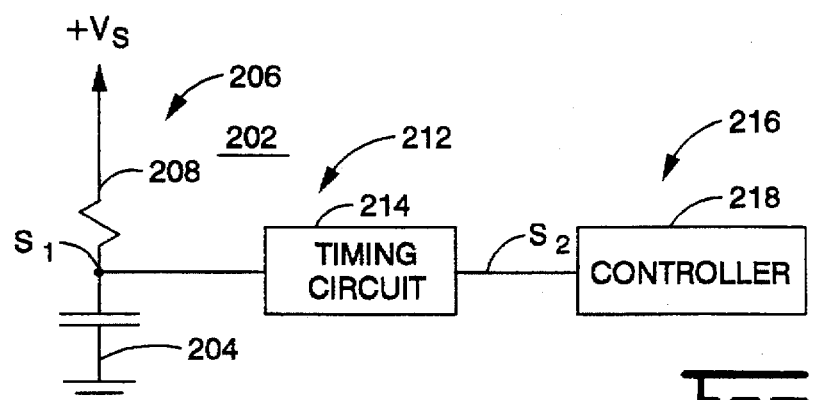
Fig_2_
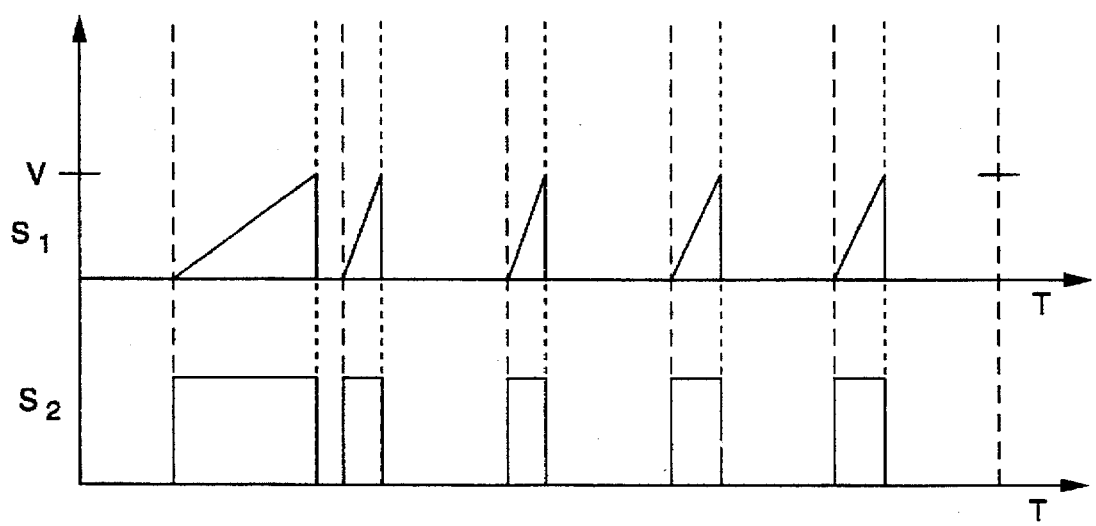
Fig_3_

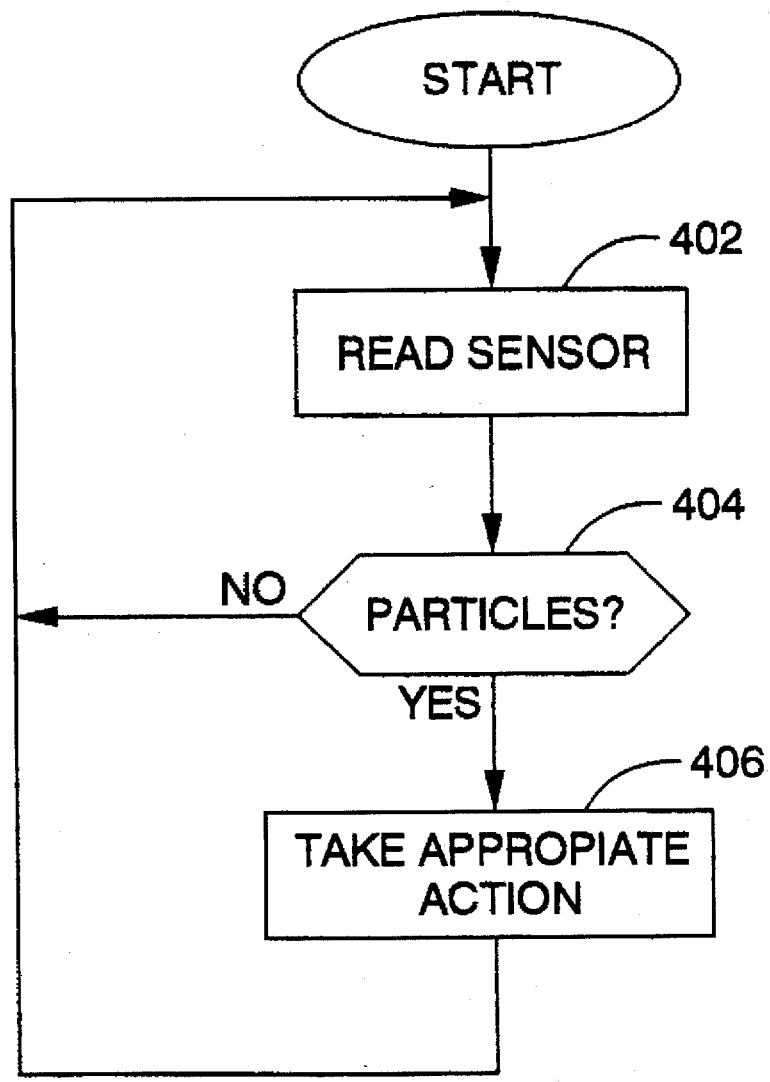
Fig_4_

CAPACITIVE PARTICLE SENSOR

TECHNICAL FIELD

This invention relates generally to hydraulic systems and more particularly to a capacitive detector which detects particles within a hydraulic system.

BACKGROUND ART

In the earthmoving industry, hydraulic systems are typically used to power earthmoving machines and/or their implements. Earthmoving machines operate in a highly hostile environment. One of the many problems that occur in hydraulic systems is contamination by ferrous particles or chips. Chips are small metallic particles which originate through the normal operation of the system. However, when chipping becomes extensive, it can seriously affect the overall reliability and life of the system. Extensive chipping may also be an indication of other serious problems in the system.

The present invention is directed to overcoming one or more of the problems, as set forth above.

DISCLOSURE OF THE INVENTION

In one aspect of the present invention an apparatus for detecting particles within a hydraulic system having a hydraulic line is provided. The apparatus includes a capacitor formed by a pair of electrodes. A charging circuit produces a charging current of constant magnitude. The charging current is used to charge the capacitor to a predetermined voltage. A timing circuit measures the elapsed time between the time at which the charging circuit begins to produce the charging current and the time at which the capacitor has been charged to the predetermined voltage. The timing circuit produces a pulse width modulated signal. The magnitude of the pulse width modulated signal is indicative of the time difference. A controller receives the pulse width modulated signal and detects particles by comparing the duration of each pulse with a reference pulse.

BRIEF DESCRIPTION OF THE DRAWINGS

FIG. 1 is a diagrammatic view of a container for containing fluid;

FIG. 2 is a block diagram of a particle sensor according to an embodiment of the present invention;

FIG. 3 is a graphical illustration of relevant signals within the pressure flow sensor of FIG. 1; and, FIG. 4 is a flow diagram illustrating operation of the particle sensor of FIG. 1.

BEST MODE FOR CARRYING OUT THE INVENTION

With reference to FIG. 1, the present invention is adapted to detect the presence of ferrous particles or chips in a hydraulic system.

With reference to FIGS. 1 and 2, the present invention, apparatus or detector 202 includes a pair of electrodes contained within a hydraulic line 102. The electrodes 104, 106 are contained within the hydraulic line 102 and are oppositely spaced so as to form a capacitor 204. The hydraulic fluid within the line 102 is the dielectric of the capacitor 204. The electrodes may be flat or curved and/or rectangular, triangular, or otherwise shaped.

A charging means 206 is connected to the capacitor 204. The charging means includes a resistor 208 and constant voltage source, $V_s$. The charging means 206 produces a charging current of constant magnitude. The magnitude of the charging current is determined by the resistor. The charging current charges the capacitor 204 until a predetermined voltage (V) across the capacitor is reached. Preferably, the resistor 208 is variable to allow for adjustment of the sensor 202. For example, an exemplar charging current, resistor value, and predetermined voltage for detecting cavitation are 2 microamps, 5 Mohms and 9 volts, respectively. The charging current will vary from system to system and will be determined to minimize or eliminate the effects of other system parameters, e.g., fluid flow, pressure, cavitation, on the charging time.

A timing means 212 is also connected to the capacitor 204. The timing means 212 includes a timing circuit 214. The timing circuit 214 detects the time at which the charging circuit begins to produce the charging current and the time at which the capacitor has been charged to the predetermined voltage. The timing circuit also produces a pulse width modulated signal. The magnitude or duration of each pulse of the pulse width modulated signal is indicative of the elapsed time between the time at which the charging circuit begins to produce the charging current and the time at which the capacitor has been charged to the predetermined voltage.

In the preferred embodiment, the timing means 212 includes a MC1555 timing integrated circuit which is available from Motorola Corp., of Schaumburg Ill. The MC1555 circuit advantageously senses when the capacitor 204 has reached the predetermined voltage and responsively discharges the capacitor into electrical ground.

A controlling means 216 receives the pulse width modulated signal from the timing means 212 and detects ferrous particles within the hydraulic fluid in the line 102. The controlling means 216 includes a controller 218 which preferably is microprocessor controlled.

With reference to FIG. 4 in the preferred embodiment, the controlling means 216 operates in accordance with a software control program. The flowchart in FIG. 4 illustrates the operation of the control program according to one embodiment of the present invention.

In a first control block 402, the sensor is read. In the preferred embodiment, the controlling means 216 includes an analog to digital converter to convert the output of the timing circuit 214 ($S_2$) to a digital signal.

In a decision block 404, the last M pulses are used to detect particles within the hydraulic system. In the preferred embodiment, particles are said to be present if the width of N of the last M pulses vary substantially from the width of the reference pulse. If particles are found to be present, control proceeds to a third control block 406. Otherwise, control returns to the first control block 402.

In the third control block 406, appropriate action is taken, i.e., detection of particles is stored as an event in a memory and/or an indicator lamp is lit.

INDUSTRIAL APPLICABILITY

With reference to FIGS. 1 and 2, the present invention is adapted to detect the presence of ferrous particles within a hydraulic system.

With reference to FIG. 3, the operation of the sensor 202 is discussed below. The charging circuit 206 produces a charging current. The charging current has a constant magnitude. The charging circuit 206 via the charging current charges the capacitor 204 until it reaches a predetermined voltage, at which time the charging current is stopped and the energy stored in the capacitor is allowed to dissipate. $S_1$ refers to the voltage across the capacitor.

The timing circuit 214 detects the time at which the charging circuit 206 begins to supply the charging current and detects the time at which the capacitor 204 has reached the predetermined voltage level. The timing circuit 214 produces a pulse width modulated signal ($S_2$). Each pulse has a duration equal to the difference between the time at which the charging circuit 206 begins to supply the charging current and the time at which the capacitor 204 has reached the predetermined voltage level.

The controlling means 216 receives the pulse width modulated signal from the timing means 212 and detects the presence of particles within the hydraulic fluid. This is accomplished by comparing each pulse to a reference. That is, a reference duration for the pulses is predetermined for the system without the particles.

As shown in FIG. 3, the existence of ferrous particles within the system will increase the charging rate and decrease the pulse width relative to the reference pulse. By using a short time constant differentiation technique between consecutive pulses, an indication of the presence of particle in the system can be obtained. Because the pulse width will display a random jitter (at a slow rate), particles can also be detected using other conventional techniques, for example, FM quadratic detection.

In the preferred embodiment, the duration of each pulse is compared to the reference duration. The controlling means 216 detects particles if N out of M pulses vary from the reference by X%. For example, if the reference duration is 100 microseconds and if out of 6 pulses in a row, 5 vary from the reference by at least 90% (pulse duration≦20 microseconds) then particles are said to exist within the system. If particles are detected, the controller may log the condition in a memory and/or signal an operator via an indicator light.

Other aspects, objects, and features of the present invention can be obtained from a study of the drawings, the disclosure, and the appended claims.

We claim:

1. An apparatus for detecting particles within a hydraulic system having a hydraulic line, comprising:

a pair of electrodes contained within the line and being oppositely spaced, forming a capacitor;

charging means, coupled to said capacitor, for producing a charging current of constant magnitude and charging said capacitor to a predetermined voltage;

timing means, connected to said capacitor, for detecting the time at which said charging means begins to produce said charging current and the time at which said capacitor has been charged to said predetermined voltage, and for producing a pulse width modulated signal, the magnitude of said pulse width modulated signal being indicative of the time between the start of said constant current and the time at which said capacitor has been charged to said predetermined voltage; and, controlling means for receiving said pulse width modulated signal, for comparing each consecutive pulse with a reference pulse, and responsively detecting particles within the hydraulic line if N pulses out of M consecutive pulses of said pulse width modulated signal vary from said reference pulse by X%.

* * * * *